US011712366B1

(12) United States Patent
Narman

(10) Patent No.: US 11,712,366 B1
(45) Date of Patent: Aug. 1, 2023

(54) ORAL THERAPY TOOL, SYSTEM, AND RELATED METHODS

(71) Applicant: MARSHALL UNIVERSITY RESEARCH CORPORATION, Huntington, WV (US)

(72) Inventor: Husnu Narman, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 17/121,121

(22) Filed: Dec. 14, 2020

Related U.S. Application Data

(60) Provisional application No. 62/947,264, filed on Dec. 12, 2019.

(51) Int. Cl.
*A61F 5/58* (2006.01)
*A61M 21/00* (2006.01)

(52) U.S. Cl.
CPC ............ *A61F 5/58* (2013.01); *A61M 21/00* (2013.01); *A61M 2021/0022* (2013.01); *A61M 2205/3331* (2013.01); *A61M 2205/3584* (2013.01); *A61M 2205/50* (2013.01); *A61M 2230/50* (2013.01); *A61M 2230/60* (2013.01)

(58) Field of Classification Search
CPC ...................................................... A61F 5/58
See application file for complete search history.

(56) References Cited

U.S. PATENT DOCUMENTS

| 5,954,673 A | 9/1999 | Staehlin et al. |
| 7,606,623 B2 | 10/2009 | Ludlow et al. |
| 7,942,782 B2 | 5/2011 | Al-Tawil |

(Continued)

FOREIGN PATENT DOCUMENTS

| CN | 103239350 A | 8/2013 |
| CN | 105228576 A | 1/2016 |

(Continued)

OTHER PUBLICATIONS https://www.arktherapeutic.com/arks-z-vibe-vibrating-oral-motor-tool/ (Year: 2015).*

(Continued)

*Primary Examiner* — Thaddeus B Cox
(74) *Attorney, Agent, or Firm* — Stites & Harbison, PLLC; Terry L. Wright; Gary N. Stewart

(57) ABSTRACT

An oral therapy tool is provided that comprises a mouthpiece including a first side and a second side, a pressure sensor operatively connected to the mouthpiece, and a microcontroller in communication with the pressure sensor. The microcontroller is configured to collect data relating to a usage of the oral therapy tool and to communicate the data to a central computer server. Systems and methods for monitoring oral therapy are further provided and collect, via a central computer server, data from the oral therapy device relating to a usage of the oral therapy device by a user. The central computer server then analyzes the data to determine the effectiveness of the oral therapy device, and transmits the analysis of the data to a remote device via a software application running on the remote device to assess and/or provide a recommended oral therapy regimen.

11 Claims, 9 Drawing Sheets

(56) References Cited

U.S. PATENT DOCUMENTS

| | | | |
|---|---|---|---|
| 8,241,035 B2 | 8/2012 | Jones et al. | |
| 8,460,159 B2 | 6/2013 | Mikhailenok et al. | |
| 9,734,292 B2 | 8/2017 | Capik | |
| 9,791,336 B2 | 10/2017 | Zhu et al. | |
| 9,855,187 B2 | 1/2018 | Martin et al. | |
| 9,911,358 B2 | 3/2018 | Ghovanloo et al. | |
| 9,990,859 B2 | 6/2018 | Salamini et al. | |
| 10,064,711 B1* | 9/2018 | Richter | A61C 17/221 |
| 10,118,037 B2 | 11/2018 | Kaula et al. | |
| 10,470,979 B2 | 11/2019 | Tepper et al. | |
| 2008/0140453 A1 | 6/2008 | Poplinger et al. | |
| 2010/0137906 A1* | 6/2010 | Stalling | A61J 11/0035 |
| | | | 606/236 |
| 2012/0322018 A1* | 12/2012 | Lowe | A61C 7/00 |
| | | | 433/6 |
| 2014/0220520 A1* | 8/2014 | Salamini | A61B 5/7455 |
| | | | 434/185 |
| 2015/0044629 A1* | 2/2015 | Wang | A46B 15/0006 |
| | | | 15/167.1 |
| 2015/0196247 A1* | 7/2015 | Lau | G01F 1/363 |
| | | | 600/301 |
| 2015/0305671 A1 | 10/2015 | Yoon et al. | |
| 2016/0154468 A1* | 6/2016 | Kimmel | G08C 17/02 |
| | | | 345/156 |
| 2016/0250054 A1* | 9/2016 | Al-Tawil | G06F 3/011 |
| | | | 345/156 |
| 2016/0296161 A1* | 10/2016 | Waller | A61B 5/4542 |
| 2017/0004731 A1 | 1/2017 | Haruta et al. | |
| 2018/0207065 A1* | 7/2018 | Tepper | A61J 17/1012 |
| 2019/0059571 A1 | 2/2019 | Jeanne | |
| 2022/0225928 A1* | 7/2022 | Lui | A61B 5/442 |

FOREIGN PATENT DOCUMENTS

| | | |
|---|---|---|
| WO | 2013163541 A1 | 10/2013 |
| WO | 2014113799 A1 | 7/2014 |
| WO | 2019/161277 A1 | 8/2019 |

OTHER PUBLICATIONS

"Introducing the all new Sensi," https://talktools.com/, (2022).

"For Speech Therapy," https://www.arktherapeutic.com/speech-therapy-tools/, (2019).

Yunusova, Yana, et al. "Positional targets for lingual consonants defined using electromagnetic articulography." http://www.probability.ca/jeff/ftpdir/yanapaper.pdf, (2012).

* cited by examiner

ORAL THERAPY TOOL, SYSTEM, AND RELATED METHODS

RELATED APPLICATIONS

This application claims priority from U.S. Provisional Application Ser. No. 62/947,264, filed Dec. 12, 2019, the entire disclosure of which is incorporated herein by this reference.

TECHNICAL FIELD

The present invention generally relates to oral therapy tools, systems, and related methods for monitoring oral therapy. In particular, certain embodiments of the present invention relate to oral therapy tools, systems, and related methods for monitoring oral therapy that integrate various sensors and/or motors with a microcontroller to monitor the use and effectiveness of an oral therapy tool and associated oral therapy.

BACKGROUND

According to research from the Centers for Disease Control and Prevention, one in twelve children ages 3-17 has had a disorder related to voice, speech, language, or swallow in the past 12 months, and only half of those children received proper intervention. Among children who have a voice, speech, language, or swallowing disorder, 34 percent of those ages 3-10 have multiple communication or swallowing disorders, while 25.4 percent of those ages 11-17 have multiple disorders. Also, the data indicate that of the 7.7 percent of children with a communication or swallowing disorder, 5 percent have speech problems, 3.3 percent have language problems, 1.4 percent have voice difficulties, and 0.9 percent have swallowing difficulties.

In many cases, speech and feeding disorders can co-occur in children, and it can get quite complicated to treat these disorders at the same time. The first important aspect of oral therapy is feeding therapy. It is used to help infants and children who have difficulties in sucking, chewing, feeding, or swallowing. The sooner these problems are addressed for children, and the sooner that those problems are treated, the better the children can grow and have a better outcome. The second aspect is speech therapy, which is a treatment for problems associated with the production of sounds or problems understanding or putting words together to communicate ideas. Since speech is one of the vital skills of humans, such speech therapy is ideally began as soon as a problem is identified. However, speech and feeding disorders can only be identified when children have reached the ages at which various speech and feeding abilities are expected. Children under the age of approximately 30 months to 36 months, for example, are often difficult to evaluate because they may be reluctant or unable to engage in formal standardized tests of their speech and feeding skills.

With that in mind, it is appreciated that the Internet of Things (IoT) is a relatively new field of research with potential for use for healthcare, especially in the therapy area. There are many definitions of the IoT, however, it can be described as a network of devices interacting with each other via machine to machine (M2M) communications through the Internet, which allows the collection and exchange of data. This technology enables automation within a broad range of industries, as well as allowing for the collection of big data. Referred as the driver of the Fourth Industrial Revolution, IoT technology has found commercial use in many areas such as air quality monitoring, smart parking solutions, precision agriculture, and forest fire detection. Extensive research has also been conducted into the use of IoT for developing intelligent systems in areas including traffic congestion minimization, structural health monitoring, crash-avoiding cars, and smart grids. Not only that, IoT-based technology is also used in many aspects of healthcare such as remote prescription, smart continuous glucose monitoring for diabetes patients, inhaler monitors for asthma patients, ingestible sensors, or Parkinson patient monitoring just to name a few. While some of the fields that were mentioned above appear somewhat different from therapy, the research conducted within them verifies the plausibility of an IoT-based healthcare system. Existing systems in other areas have proven that remote monitoring of objects, with data collection and reporting, are achievable. This can, therefore, be expanded and adapted for monitoring the health or healing progress of people and reporting it to relevant parties such as nurses, doctors, emergency services, parents, and healthcare centers.

As suggested above, in the field of oral therapy, according to the statistics of the National Institute of Deafness and Other Communication Disorders (NIDCD), only 50 percent of children with some form of oral disorders such as voice, speech, language, and swallowing receive proper treatment. Currently, in the market, there are several companies that produce oral therapy tools. Many current tools are not smart or connected. Some of the tools are capable of data collection, but are limited in terms of auto-evaluations and detecting the feeding and speech intervention requirements. As a result, customers do not have many choices in the market. On the other hand, the available tools for treatment on the market right now are quite expensive, which ranges from $30-$2000 and are somewhat fragile. Not only that, the cost of going to a therapist and booking therapy sessions are also quite high. Usually, a patient would need several sessions since that is the only way for the therapists to tell if the patients are making progress.

Accordingly, a smart therapy device configured to help children and other individuals exercise oral functions and also monitor the biomedical signals and assess their progress over time is needed. In particular, a device that can communicate with cloud services and other mobile environments with intensive data acquisition, while also assessing whether exercises are effective and identifying if the users need more attention would be both highly desirable and beneficial.

SUMMARY

The presently-disclosed invention includes oral therapy tools, systems, and related methods for monitoring oral therapy. In particular, certain embodiments of the present invention include oral therapy tools, systems, and related methods for monitoring oral therapy that integrate various sensors and/or motors with a microcontroller to monitor the use and effectiveness of an oral therapy tool and associated oral therapy.

In some embodiments of the present invention, an oral therapy tool is provided that includes a mouthpiece including a first side and a second side, and a pressure sensor operatively connected to the mouthpiece. Additionally included in the oral therapy tool is a microcontroller that is in communication with the pressure sensor and is configured to collect data relating to a usage of the oral therapy tool and to communicate the data to a central computer server.

The oral therapy tool is generally configured to stimulate and exercise a user's oral muscles more effectively. In this regard, an exemplary oral therapy tool, in some embodiments, further includes a vibrating motor that is operatively connected to the mouthpiece and provides sensory stimulation to a user at the mouthpiece. The oral therapy tool can further comprise a temperature sensor for monitoring a temperature adjacent to the mouthpiece. In some embodiments, the first side of the mouthpiece, the second side of the mouthpiece, or both include a raised texture. For instance, in certain embodiments, the first side of the mouthpiece includes a first raised texture, while the second side of the mouthpiece includes a second raised texture that can be the same as or different from the first raised texture.

In addition to serving to stimulate and exercise a user's oral muscle, the pressure sensors included in an exemplary oral therapy tool are generally configured to monitor the use of the tool, and more particularly, to monitor the pressure applied to the tool over an amount of time. Such pressure sensors can, in certain embodiments, be in the form of a resistive sensor configured to measure the amount of changes in electrical resistance when force is applied to the sensor. In some embodiments, such pressure sensors can be incorporated directly into the mouthpiece or, in other embodiments, are operably connected to the mouthpiece through various means for transmitting the amount of applied pressure. For instance, in some embodiments, the mouthpiece defines a plurality of hollow chambers in an interior of the mouthpiece with each of the hollow chambers operably connected to the pressure sensor via a pressure-transmitting tubing.

Regardless of the particular configuration of the pressure sensors, once an applied force is detected by the pressure sensors, the microcontroller included in an exemplary oral therapy tool, as indicated above, receives data from the various pressure sensors related to a usage of the oral therapy tool and is configured to transmit that data to a central computer server (e.g., by wired or wireless communication). In this way, in some embodiments, the exemplary oral therapy tools described herein can be included and made use of in a larger system for monitoring oral therapy that further comprises a central computer server in communication with the oral therapy tool and a database in communication with the central computer server. In such a system, the database can be configured for storing data relating to a usage of the tool, such that a query of the data related to the usage of the tool can be initiated from a remote device (e.g., a smart phone) and then communicated to the remote device from the central computer server via a software application running on the remote device to thereby provide information relating to the usage of the tool to the remote device. Such data relating to the usage of the device can, in certain embodiments, include session and/or minute-by-minute averages of an amount of pressure applied to the tool, a frequency of pressure applied to the tool, and/or a temperature within an oral cavity of a user.

Further provided by the present invention are methods for monitoring oral therapy. In some embodiments, a method for monitoring oral therapy is provided in which data is first collected from an oral therapy device, via a central computer server, that relates to a usage of the oral therapy device by a user. The central computer server then analyzes the data related to the usage of the device to determine the effectiveness of the oral therapy device and transmits to a remote device the analysis of the data via a software application running on the remote device. In some implementations of the method, the collected data from the oral therapy device comprises data collected from the oral therapy device at a first time point and a second time point. In some implementations, the collected data is from multiple oral therapy devices, which, in turn, can be analyzed to provide a recommended oral therapy regimen.

Further features and advantages of the present invention will become evident to those of ordinary skill in the art after a study of the description, figures, and non-limiting examples in this document.

DESCRIPTION OF EXEMPLARY EMBODIMENTS

The present invention includes oral therapy tools, systems, and related methods for monitoring oral therapy. In particular, the present invention includes oral therapy tools, systems, and related methods for monitoring oral therapy that integrate various sensors and/or motors with a microcontroller to monitor the use and effectiveness of an oral therapy tool and associated oral therapy.

In some embodiments, the present invention is based, at least in part, on the development of an oral therapy tool that integrates sensors and a Wi-Fi-enabled microcontroller into the therapeutic tool along with an algorithm to overcome the sensory issues which are related to the practice times commonly observed in oral therapy tools so as to give better feedback on a user's progress. In particular, the tools, systems, and methods described herein provide the ability: to follow the user's progress by making use of pressure and heat or temperature sensors and by collecting data with the tool and sending it to the Cloud via wireless communications; to display progress reports through the use of an algorithm that collects and correlates data with practice time and speed; to make the data more accessible and beneficial via a user-friendly smart-phone application that allows health-care providers and users the ability to sort, calculate, filter the data or compare it with other user's data to come up with their assessments; and to test the efficiency of the device and the created application with the algorithm, such that the data collection from the sensors and the time to transfer the collected data from the device to cloud platform can be analyzed. Moreover, by making use of the oral therapy tools, systems and methods described herein, users, parents, and/or therapists can monitor the user's progress in real time and assess whether the exercises performed by the users are effective.

Figure 9:
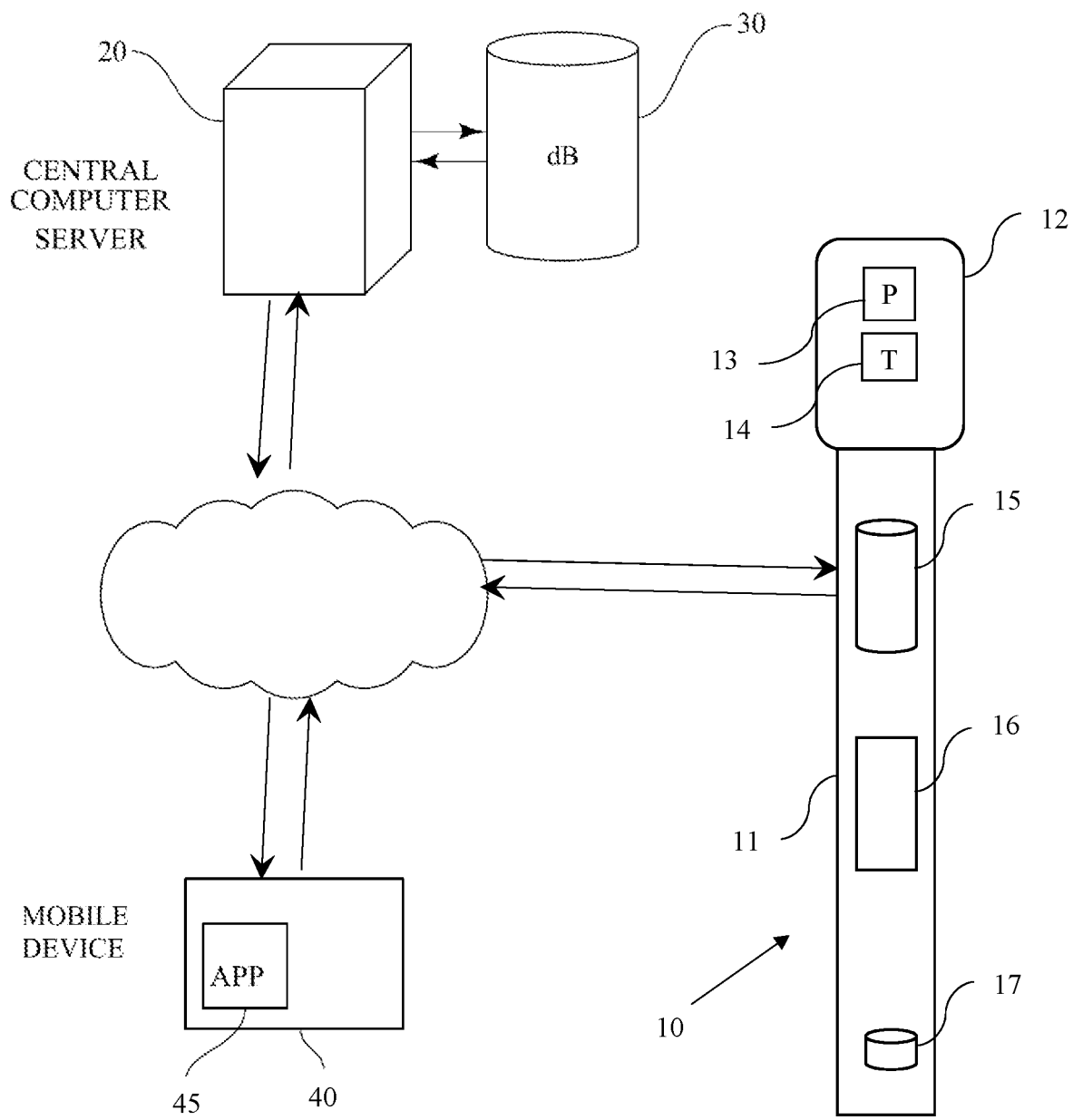
FIG. 9 is a schematic diagram showing an exemplary oral therapy tool and system in accordance with one embodiment of the present invention.

In some embodiments of the present invention, and referring generally to FIG. 9, an oral therapy tool 10 is thus provided that includes a hand piece 11 including a mouthpiece 12 having a first side and a second side. The oral therapy tool 10 further includes a vibrating motor 15 that is operatively connected to the mouthpiece 12 and is configured to provide sensory stimulation to a user at the mouthpiece 12 of the hand piece 11. A pressure sensor 13 is further included in and operably connected to the mouthpiece 12 to monitor the amount of pressure applied to the tool 10, along with a temperature sensor 14 to measure the temperature adjacent to the tool 10 (e.g., in the oral cavity of a user). Additionally included in the tool 10 is a battery 17 for powering the tool 10, as well as a microcontroller 16 that is in communication with at least the pressure sensor 13 and temperature sensor 14, and that is configured to collect data relating to a usage of the tool 10 and to communicate that data to a central computer server 20, as described in further detail below.

With further respect to the oral therapy tool 10, the oral therapy tool 10 and its associated vibrating motor 15 are configured to stimulate and exercise a user's oral muscles more effectively. In this regard, the mouthpiece 12 generally includes a raised texture on a first side, a second (i.e., opposite) side, or both. For example, in one embodiment of the oral therapy tool 10, the mouthpiece 12 has a rectangular shape with a first raised texture (e.g., a bumpy texture) on a first side, and a second raised texture (e.g., a striated texture) on a second side. Without wishing to be bound by any particular theory or mechanism, it is believed that such textured surfaces provide tactile input, awareness, and sensation for users of the tool 10 and can be used to stimulate the gums, palate, lips, cheek, and tongue by tapping, stroking, and applying gentle pressure.

Figure 3:
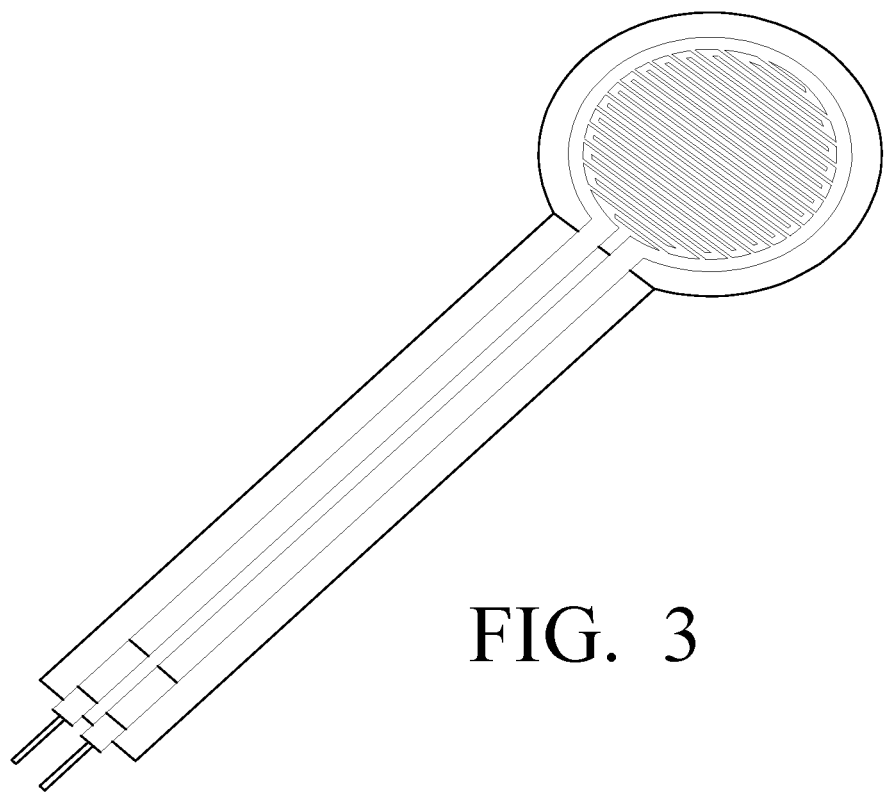
FIG. 3 is an image showing a round force sensitive resistor used in accordance with an exemplary oral therapy tool of the present invention.

To collect data associated with the use of the tool 10, the tool 10 includes low-power sensors, including the pressure sensor 13 and temperature sensor 14. The pressure sensor included in the oral therapy tool 10 of the present invention will typically be exposed to a significant amount of pressure, but is also selected such that it can be incorporated in the tool 10 in a manner that is affordable, small, replaceable, and stable. For example, in certain embodiments, the oral therapy tool 10 includes a pressure sensor 13 in the form of a Round Force-Sensitive Resistor (FSR)-Interlink 402 (see, e.g., FIG. 3), that allows for the detection of physical pressure by changing its resistive value (in ohms) in response to how much it is pressed.

Figure 4:
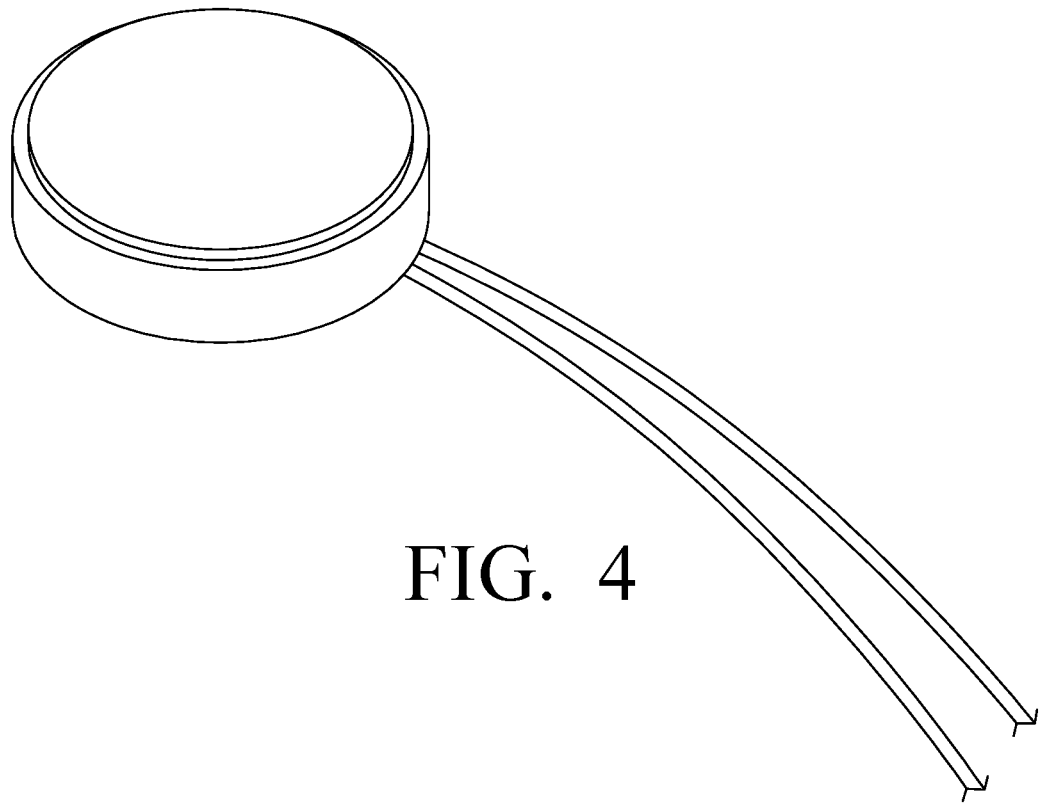
FIG. 4 is an image showing a vibrating mini motor disc used in accordance with an exemplary oral therapy tool of the present invention.

Turning now to the vibrating motor 15 included in the exemplary oral therapy tool 10, the vibrating motor 15 also assists in providing tactile oral cues, in directing the articulators, in stimulating the oral muscle, in increasing oral awareness and tone, and in decreasing mouth stuffing, drooling, oral defensiveness, and texture aversions. Not only that, the gentle vibration from the vibrating motor 15 provides a sensory stimulation that can increase oral focus and draw more attention from the users to their lips, tongues, cheeks, and jaws. Moreover, the motor 15 is also FDA compliant as it includes no lead, phthalates, PVC, BPA, or latex. An exemplary vibrating motor 15 capable of being used in an exemplary oral therapy tool is shown in FIG. 4.

Figure 5:
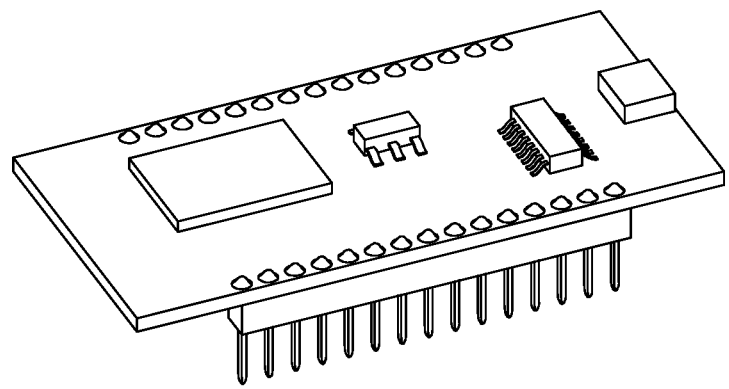
FIG. 5 is an image showing an exemplary microcontroller used in accordance with an exemplary oral therapy tool of the present invention.

Referring now to FIGS. 5 and 9, the microcontroller 16 included in the oral therapy device is configured to provide IoT ability and is thus generally a WiFi-enabled microcontroller that is small, compact, cost-effective for mass production, and configurable for future updates. Such microcontrollers include, but are not limited to, microcontrollers such as Spark Photon, NodeMCU, and Pro Micro ESP8266 microcontrollers, as each of those microcontrollers include significant computing ability, support full TCP/IP stack and partial Secure Sockets Layer (SSL), small size, and an affordable price. In some embodiments, the microcontroller 15 is a NodeMCU microcontroller (see, e.g., FIG. 5) as such a microcontroller provides a robust CPU, is affordable, has built-in Wi-Fi compatibility, and provides for the ability to integrate an IoT application into the tool 10. Furthermore, in such embodiments, the NodeMCU consumes just a minimal amount of power and can run on the battery 17 (e.g., 9V) included in the tool 10, which makes it versatile and flexible in many situations.

By making use of the oral therapy tool 10 described herein above, including the WiFi-enabled microcontroller 16, the tool 10 can thus be used to monitor the progress of a user anywhere, anytime as long as the tool 10 is able to access an Internet connection. Such remote use and monitoring of therapy can allow the user to save the time, money, and effort on booking appointments with therapists, driving to appointments, and having checks every week to see if they are making progress, which is particularly beneficial for those users who live in rural areas or do not have transportation. Such monitoring also provides a much easier way for a health care provider to access all of a user's data, which would give a better picture of the user's progress.

Figure 1:
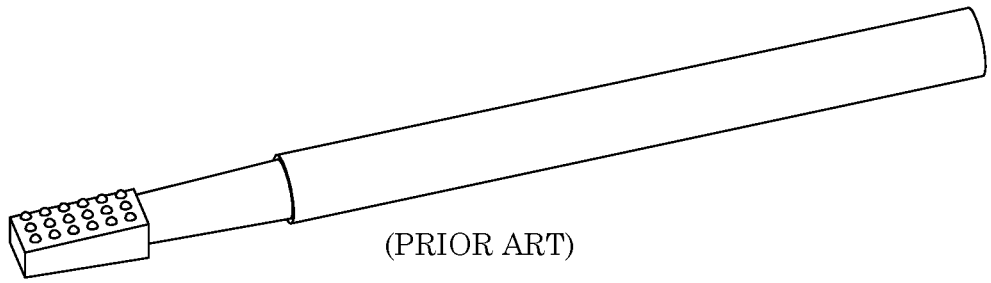
FIG. 1 is an image showing a prior art oral motor tool for therapy manufactured by Ark Therapeutics Services, Inc. (Columbia, SC).
Figure 2:
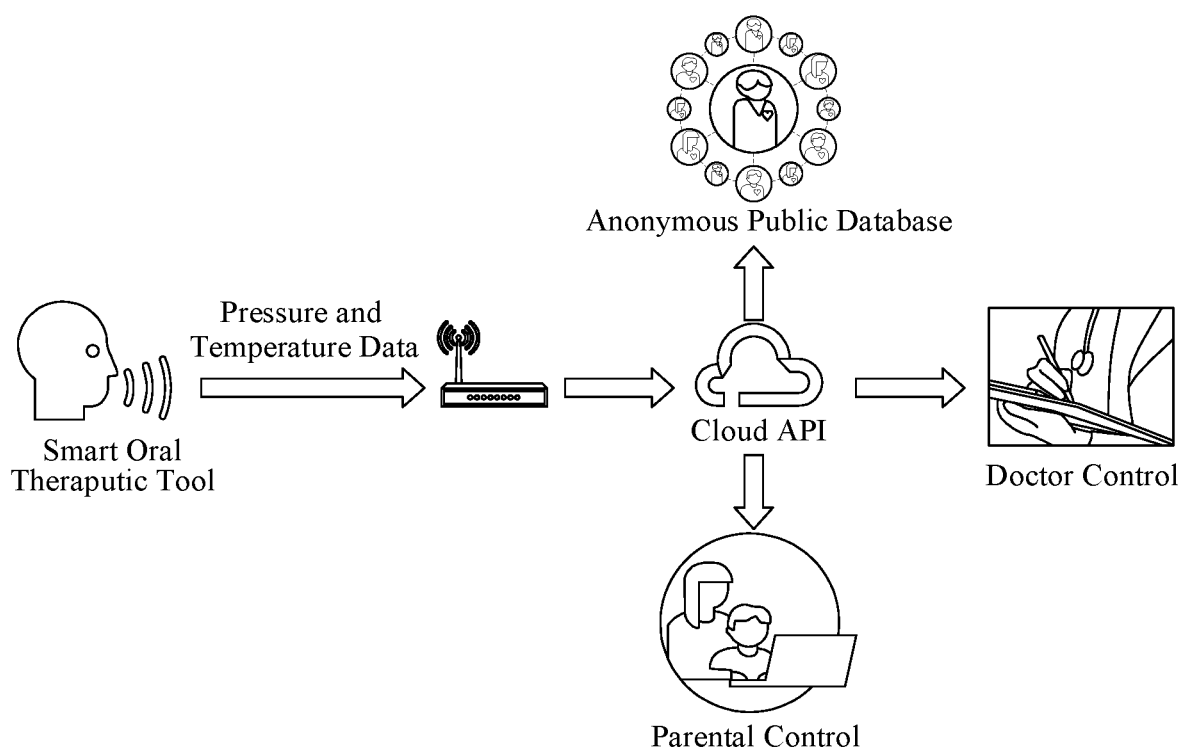
FIG. 2 is a schematic diagram showing an exemplary system for monitoring oral therapy in accordance with one embodiment of the present invention.
Figure 6:
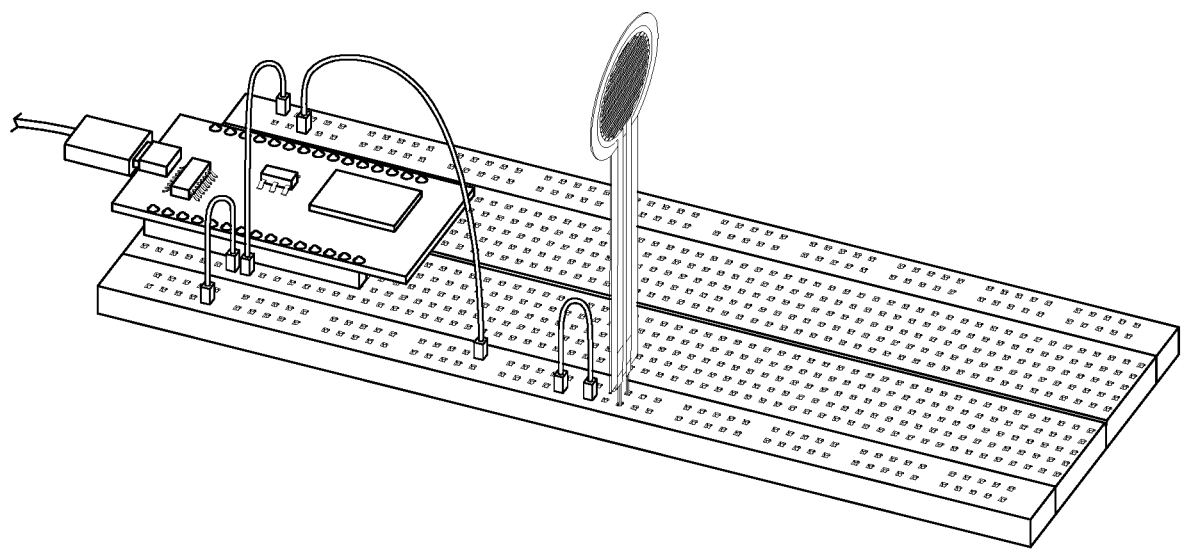
FIG. 6 is an image of an exemplary oral therapy tool of the present invention in accordance with one embodiment of the present invention.

In this regard, and referring now to FIGS. 2 and 6, in some embodiments, the exemplary oral therapy tool 10 is included in a system and method for monitoring the oral therapy of a user. In the system, the oral therapy tool 10 is in communication with a central computer server 20 and associated database 30, which may be a physical database or a virtual, cloud-based database. The central computer server 20 is also in communication with one or more remote (e.g., mobile) devices 40 as described in further detail below. As indicated above, such communications between the central computer server 20 and the oral therapy tool 10, as well as between the central computer server 20 and the remote devices 40, are generally facilitated through a wireless internet connection, but it is of course contemplated that additional means of communication including satellite communications, or other communications network or similar known means of data transport can also be utilized. Moreover, in some implementations, it is also contemplated that at least some users can also be in communication with the central computer server 20 and associated database 30 via a remote device such as a desktop or personal computer with a software component that communicates with the central computer server 20, such as via a web-based application accessible through a common internet browser program.

In using the oral therapy tool 10 (see, e.g., FIG. 6 showing an exemplary oral therapy tool of the present invention including a pressure sensor and the NodeMCU microcontroller), as the microcontroller 16 has the ability to connect to the internet via wireless communications (i.e., WiFi), the oral therapy tool 10 sends the data directly into the cloud, where it is then received by the central computer server 20. In this way, the data transmitted by the tool 10 relating to the usage of the device can be analyzed by the central computer server 20 to determine the effectiveness of the oral therapy tool 10. For example, in some embodiments, the data related to the usage of the tool 10 that is transmitted to the central computer server 20 can include session and minute-by-minute averages of an amount of pressure applied to the tool 10, a frequency of pressure applied to the tool 10, and a temperature within an oral cavity of a user. As another example, in some implementations, the data related to the usage of the tool 10 and collected by the central computer server 20 can include collecting data from the oral therapy tool 10 at a first time point and a second time point such that the two time points can be compared and to determine the overall effectiveness of the tool 10 in providing oral therapy and/or to determine whether any progress is being made with the user's therapy.

To assess the performance and effectiveness of the use of the oral therapy tool 10, in some implementations, data relating to the pressure, intensity, and temperature that is collected through the device is then analyzed by the central computer server 20 using an algorithm. Such algorithms include, for example, the Algorithm 1 provided below, and which uses two parameters, namely dynamic sensory thresholds and the average activity frequency per minute, to track the progress. In some implementations, while measuring the progress, the speed decrement rate due to the tiredness is also considered to provide a reliable evaluation.

In some implementations, to make use of an exemplary oral therapy tool of the present invention and monitor oral therapy, a first time user will have an "entry practice session" to collect the base performance of the user. Over the next sessions, if the performance is not improved more than a certain percentage or if the user is losing skills, the exercise or oral therapy can then be identified as ineffective. It is also possible that the activity can increase sensitivity more than the expected amount. In such situations, a therapist prescribing the therapy can then respond accordingly to the result.

| Algorithm 1 Algorithm for data analysis for personalization |
|---|
| Input: Collected data [ ] {For each minute} |
| Report: Reports for each minute [ ] {Report can be custom range} |
|     Initialization : |
| 1:    x = calculateIndividualizedThresholdsforSenses( ) {From initial practice and average of the previous collected data} |
| 2:    y = findSlownessAndWeaknessTimeInMinute( ) {Speed decrement in every minute from the previous collected data} |
|     LOOP Process |
| 3:    for i = 0 to collectedDatalength do |
| 4:      if($\|data[i] - y\| \leq x$) then |
| 5:        Reports[i] = Need Improvement |
| 6:      else if ($\|data[i] - y\| == x$) then |
| 7:        Reports[i] = No Changes |
| 8:      else if ($\|data[i] - y\| >= 2 * x$) then |
| 9:        Reports[i] = High Sensitivity |
| 10:     else |
| 11:        Reports[i] = Regular Improvement |
| 12:     end if |
| 13:    end for |
| 14:    return Reports |

Figure 7:
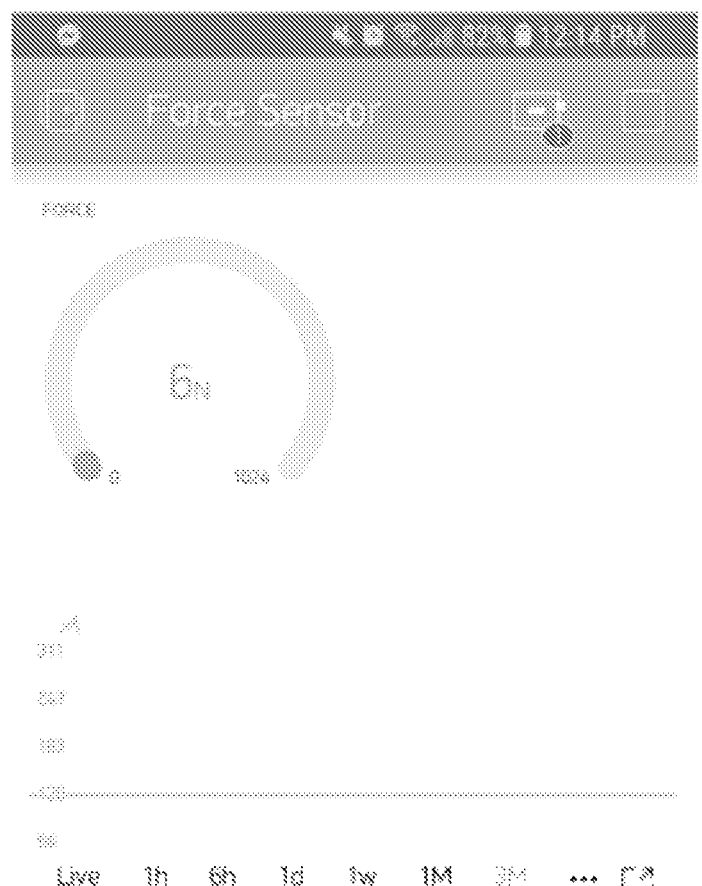
FIG. 7 is a screenshot of a software application ("app") running on a mobile device and showing an exemplary graphical user interface of a pressure sensor included in an exemplary oral therapy tool of the present invention.

To provide the user, a therapist, or other individual with access to the data analyzed by the central computer server 20, a query of the data related to the usage of the tool is initiated from a remote or mobile device 40 (e.g., a smart phone) and the analyzed data is communicated/transmitted to the remote device 40 from the central computer server 20 via a software application 45 running on the remote device to thereby provide information relating to the usage of the tool 10 to the remote device 40. In this regard, the user, therapist, or other individual generally installs the software application (or "app") 45 on the remote (e.g., mobile) device 40 to allows the user to use and interact with the analyzed data via communications with the central computer server 20. Of course, such remote or mobile devices include, but are not limited to, smartphones, tablets, or similar computing device with a microprocessor, an internal memory component (e.g., a hard drive or solid-state drive), and a display screen that allow the data from the sensors 13, 14 and related components to be viewed in the mobile application. For instance, as shown in FIG. 7, the mobile application on a remote device can allow the pressure results from the tool 10 to be observed in graph format, where live data can be observed with 1-2 second delays for pressure. Moreover, by making use of such remote devices and apps in the systems described herein, hourly, six-hourly, daily, weekly, monthly, three monthly, yearly, and all pressure activities can be observed from the mobile application. Similarly, temperature and frequencies of the activities can be observed as well.

In some implementations, data from the oral therapy device comprises collecting data from multiple oral therapy devices and then storing the data from those multiple oral therapy devices in the database 30. Subsequently, upon the analysis of the data from the multiple oral therapy devices, the collective data can be used to identify and provide a recommended oral therapy regimen to a user that is predicted to be most effective for that particular user in view of the collective data and/or the condition of the user.

With further respect to the central computer server 20 used in accordance with the present invention, it should be readily apparent to one of ordinary skill in the art that software running on the central computer server 20 causes computer-readable instructions stored in a memory component of the central computer server to be executed by a microprocessor of the central computer server 20. Similarly, with respect to the app, it should be readily apparent to one of ordinary skill in the art that the app causes computer-readable instructions stored in the memory component of the smartphone, tablet, or other remote device to be executed by the microprocessor of the of the smartphone, tablet, or other computing device. In view of the foregoing description of the system and method of the present invention, such computer-readable instructions can be readily coded into computer readable form using standard programming techniques and languages by one of ordinary skill in the art.

Figure 10:
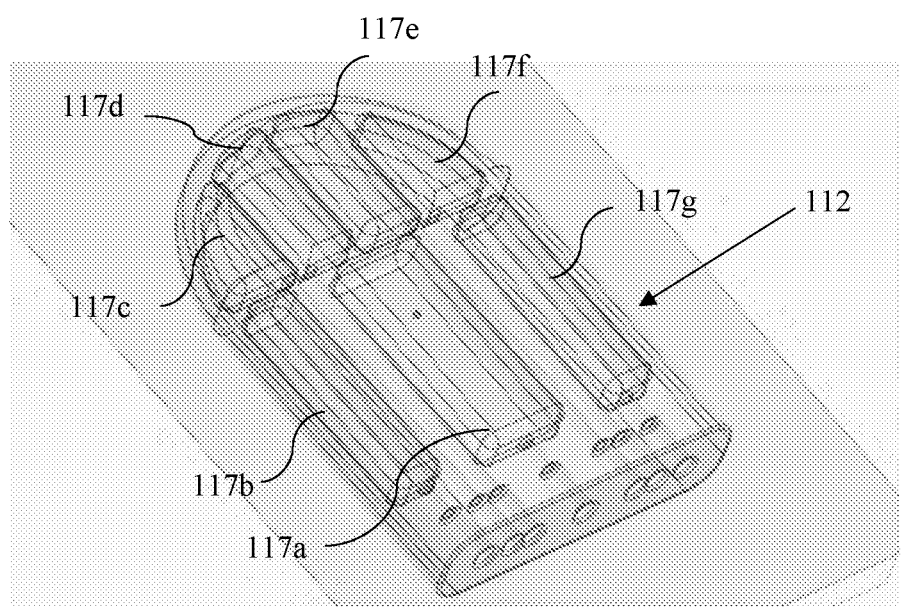
FIG. 10 shows an exemplary mouthpiece for use in an oral therapy device made in accordance with the present invention and including a plurality of hollow chambers.
Figure 11:
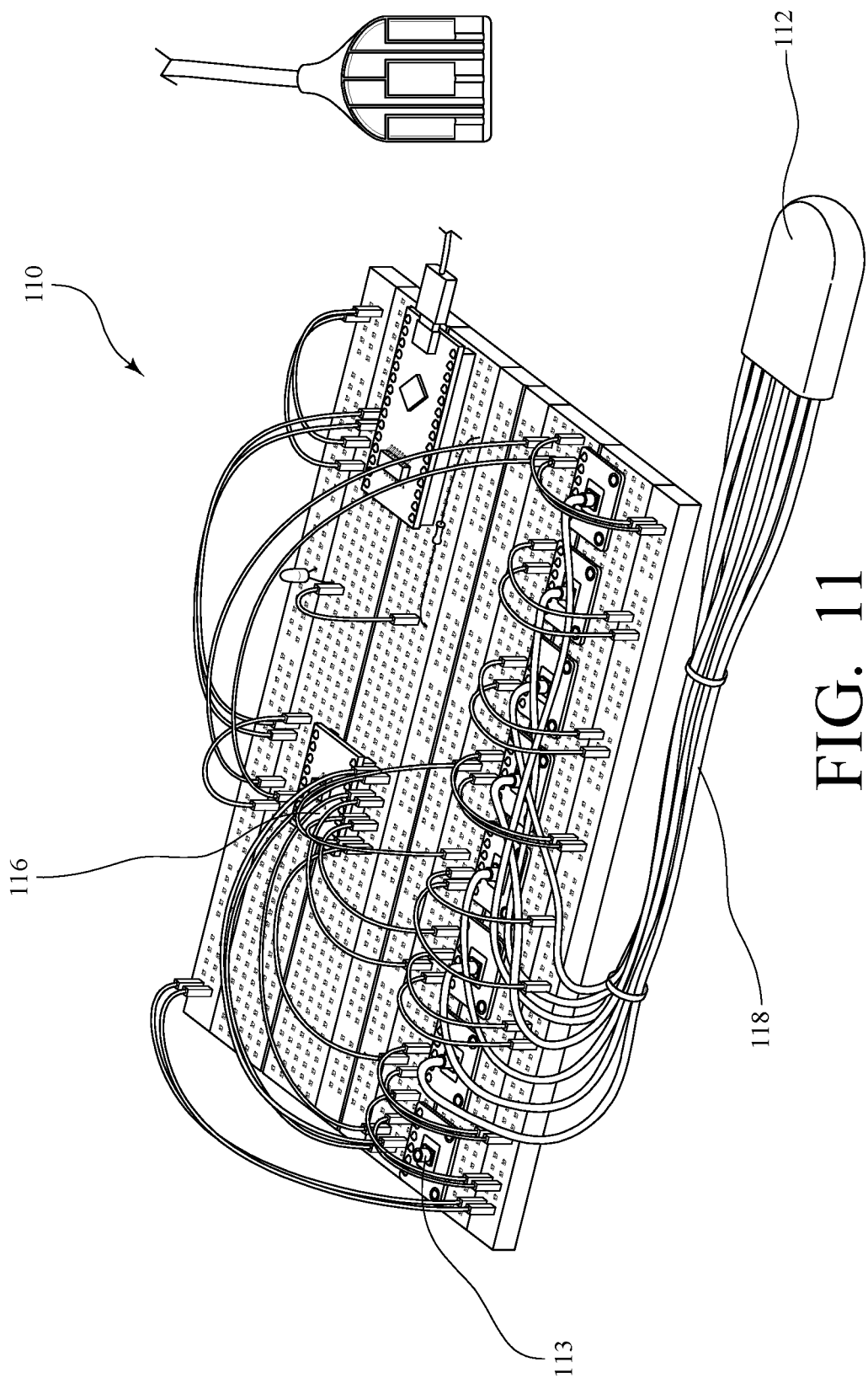
FIG. 11 is an image showing another exemplary oral therapy tool of the present invention in accordance with another embodiment of the present invention and making use of the mouthpiece shown in FIG. 10.
Figure 12:
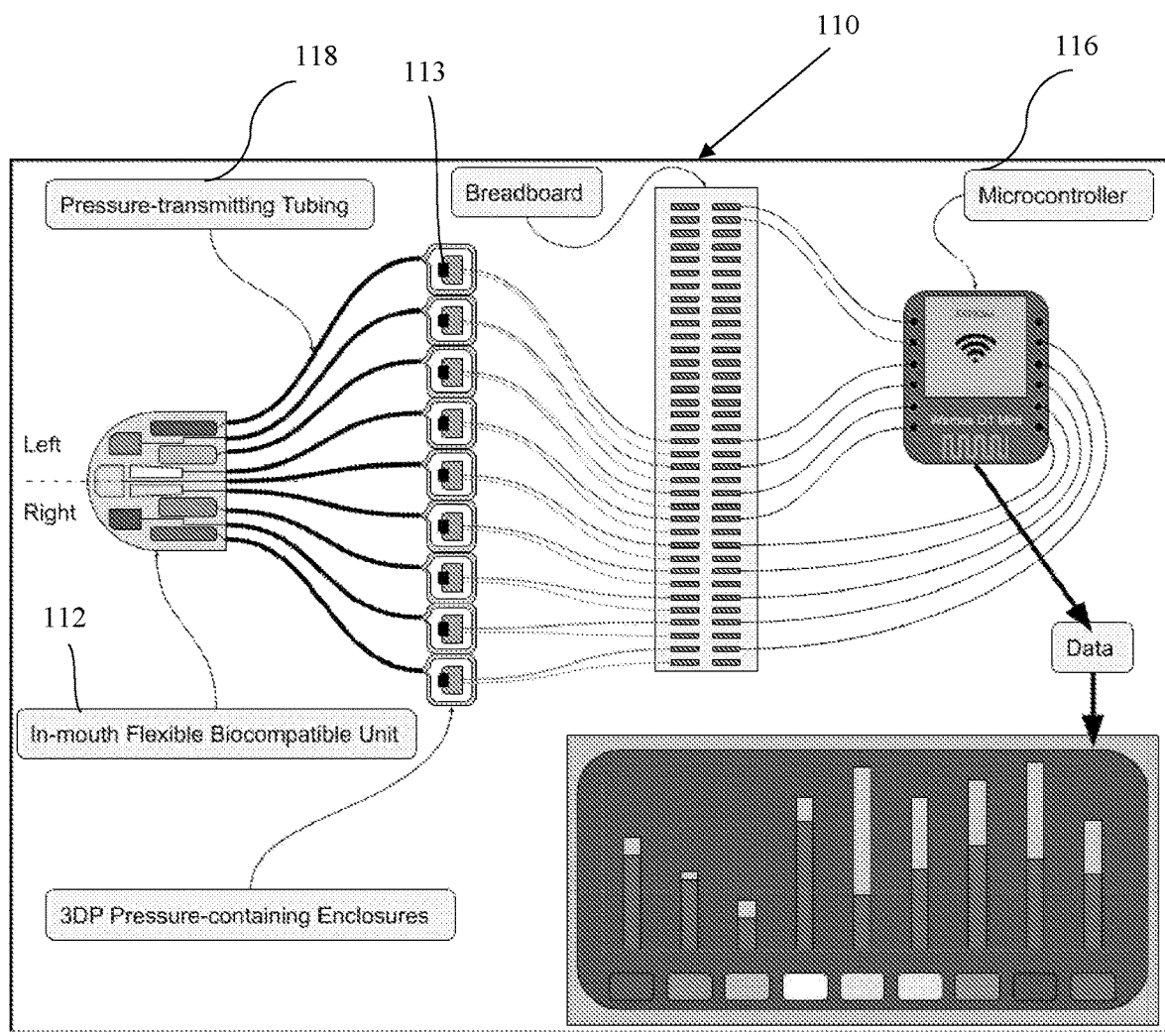
FIG. 12 is a schematic diagram showing another exemplary oral therapy tool and system in accordance with the embodiment of the present invention shown in FIGS. 10-11.

Finally, although the above-described systems and methods for providing and monitoring oral therapy have been described with reference to the exemplary features shown in FIGS. 3-6 and 9, it is further contemplated that different configurations and arrangements of those features can also be utilized to produce an exemplary oral therapy tool and/or system capable of collecting data and being made in accordance with the present invention. For instance, and referring now to FIGS. 10-12, in another embodiment of the present invention, an oral therapy tool 110 is provided that makes use of a mouthpiece 112 comprised of a flexible biocompatible material and defining a plurality of hollow chambers 117a-g in an interior portion of the mouthpiece 112. Each of the hollow chambers 117a-g are separate from each other and are individually connected to a corresponding one of a plurality of pressure sensors 113 via pressure transmitting tubing 118. In this way, when the mouthpiece 112 is inserted into the mouth of a user and pressure is applied to a particular area of the mouthpiece 112, an increase in pressure in a particular one or more of the hollow chambers 117a-g is communicated to the corresponding one or more of the pressure sensors 113. To collect the data associated with the use of the oral therapy tool 110, each of the pressure sensors 113 are then connected to and communicate with a microcontroller 116 that collects and subsequently transmits the data, as depicted in FIG. 12, to a central computer server in the manner similar to that described herein above with reference to FIGS. 1-9.

The presently-disclosed subject matter is further illustrated by the following specific but non-limiting examples.

EXAMPLES

To analyze the effectiveness of an exemplary oral therapy tool of the present invention, experiments were undertaken using the exemplary device shown in FIG. 6. Table 1 shows us the data recorded from an eight-year-old child exercised oral therapy with the oral therapy tool at different time intervals. The table presents the results of the oral therapy tool as it calculated average pressure, frequency, temperature for every minute in each session. Ideally, the sensors and NodeMCU collect and compute all of the data above, then pack the data into a packet and send it to the Cloud (application programming interface) API through Wi-Fi under the TCP/IP API. The time it takes to transfer each data packet to the cloud might vary. However, as the average internet upload speed in the U.S. is 40.28 Mbps over fixed broadband and 9.90 Mbps over mobile, the upload rate will have a delay of only about 0.7 seconds to compute, upload, and display the data in the database or other mobile devices. In this regard, the initial experiments used 25/10 (download 25 Mbps, upload 10 Mbps) and 300/180 Mbps (download 300 Mbps, upload 180 Mbps) speed in shared Wi-Fi networks to test the communication speed. To obtain credible results, the delay time was evaluated at different times during the day. The average delay observed in the prototype was 0.93 seconds.

Figure 8:
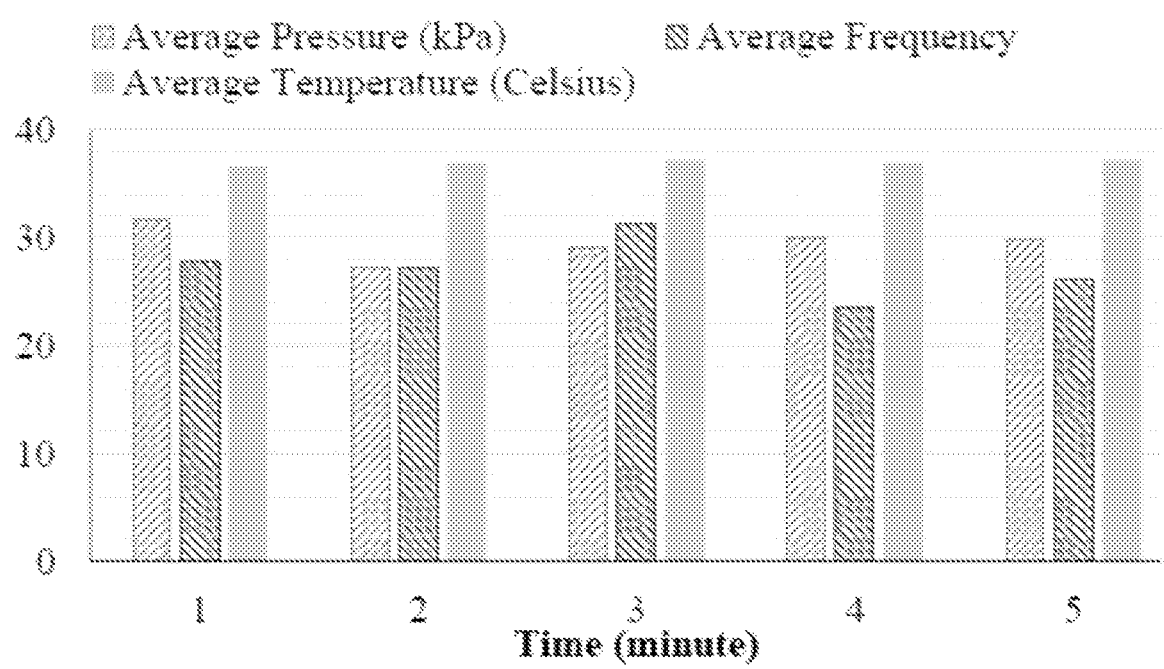
FIG. 8 is a graph showing the average results for each session duration splitting the session to minutes and generated through use of an exemplary oral therapy tool of the present invention.

FIG. 8 shows the average results which are obtained from the tool for 1 to 5 minutes of testing sessions. Although the average pressure amount and the frequency of activities information that was obtained was helpful for overall session effectiveness, the observed results were not helpful for the session itself. Since such patient loses their attention, it was not possible to understand how long the patient can focus from the session-based average results. Therefore, the developed tool provide not only session average but also each minute average as shown in Table 1.

In Table 1, the results obtained from the tool are presented for 1 to 5 minutes of testing sessions. The average pressure and the number of pressing frequencies were also measured for each minute although the testing sessions are longer than one minute. As explained in Algorithm 1, patients can get tired because of the activity. Therefore, the pressure and speed can decrease in each minute. Such changes can be more obvious when the session duration is increased. For example, for this eight-year-old child, 5 minutes session shows slightly tiredness because the average pressure and the number of time pressure applied slightly decrease. Moreover, the same strategy can be used to find the attention time for the patients to arrange the session duration for the activity.

TABLE 1

Average Pressure, Frequency, Temperature in Different Time Intervals.

| Time(Minute) | 1 | 2 | 3 | 4 | 5 |
|---|---|---|---|---|---|
| Average Pressure (kPa) (The pressure was averaged in each minute) | | | | | |
| 1 | | | 31.64 | | |
| 2 | | 29.18 | | 25.42 | |
| 3 | | 31.56 | 26.85 | 28.77 | |
| 4 | 27.95 | 34.75 | 30.12 | | 27.56 |
| 5 | 32.5 | 33.0 | 29.3 | 27.7 | 27.0 |
| Average Frequency (Number of time pressure was applied in one minute) | | | | | |
| 1 | | | 27.83 | | |
| 2 | | 26.14 | | 28.14 | |
| 3 | | 32.01 | 27.15 | 34.88 | |
| 4 | 24.1 | 24.46 | 23.75 | | 21.77 |
| 5 | 26.6 | 28.4 | 28.6 | 21.1 | 25.5 |
| Average Temperature (Celsius) | | | | | |
| 1 | | | 36.54 | | |
| 2 | | 37.22 | | 36.68 | |
| 3 | | 37.05 | 37.44 | 37.21 | |
| 4 | 36.71 | 36.96 | 37.21 | | 37.01 |
| 5 | 37.2 | 37.3 | 37.0 | 37.4 | 37.2 |

As described above, an oral and, in particular, a speech and feeding therapy tool has been developed to easily monitor and track the progress of the patients, and has been tested in the cloud API under various network environments. The device has also been tested using different time intervals during the day to test its stability and reliability. The developed tool and applications will help the parents and/or doctors to assess and follow the users easily and effectively. Moreover, by making use of the oral therapy tools described herein, the oral therapy tools not only allow for the collection of data, but further allow for the assessment and improvement in a number of oral developments areas, including jaw strength and tongue position/movement. Indeed, to assess the oral development of a child for swallowing and speech development, a number of factors play an important role. Jaw strength and tongue position, however, are two important factors for oral development that need to be analyzed continuously.

One of the important aspects of chewing (bite force) development for infants and toddlers is the jaw and related muscles. Muscles involved in mastication (chewing) include the Masseter, Temporalis, Lateral pterygoid, and Medial pterygoid. The present oral therapy tools can assist in the measurement of the strength of the bite. This is important for identifying disorders and assisting the child's transition to solid foods (meats, raw vegetables, hard cookies, and crackers) that are not meltable (cheese and soft cooked vegetables).

Likewise, with respect to tongue position and/or movement, the tongue begins the coordinated movement in utero at approximately 20 weeks. Infants and toddlers often have difficulty with tongue coordination for suck, swallow, and breath patterns if they have any disorders. If the restrictions of tongue movements are not severe, infants can often obtain enough nutrition until they are 1 or 2 years of age, when they should be transitioning to solid foods. However, they cannot obtain enough nutrition due to the tongue's inability to move laterally to place the foods on their molars for chewing. Additionally, these infants gag when the food is pushed posteriorly in the mouth. Therefore, measuring the tongue movement will help understand the readiness for non-nutritive and nutritive sucks and chewing. Moreover, measuring how strong and long the latch will help educate pediatricians, otolaryngologists, and lactation consultants and determine when a frenectomy (tongue release) is necessary. Tongue movements are also vital to produce sounds, although it is not well-known the relation between tongue strength and speech disorders. Due to the multiple pressure sensors included in some embodiments of the present invention, the oral therapy tool described herein allows for the tongue movement to be tracked.

Moreover, through the continuous collection of data by the oral therapy tools and systems of the present invention, the exemplary oral therapy tools and systems allow users, therapists, and other involved individuals: 1) to compare the skills children have with their tongue during non-speech and non-feeding tasks to those they do or do not have during feeding and speech tasks; 2) to understand the development process over time; 3) to understand the benefits of therapy sessions and identify the most helpful strategies in the therapies; and 4) to justify the need for continued service for children in case insurance companies do not want to pay for services.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1 Y. J. Fan, Y. H. Yin, L. Da Xu, Y. Zeng, and F. Wu, "Iot-based smart rehabilitation system," IEEE transactions on industrial informatics, vol. 10, no. 2, pp. 1568-1577, 2014.
2. S. R. Islam, D. Kwak, M. H. Kabir, M. Hossain, and K.-S. Kwak, "The internet of things for health care: a comprehensive survey," IEEE Access, vol. 3, pp. 678-708, 2015.
3 D. V. Dimitrov, "Medical internet of things and big data in healthcare," Healthcare informatics research, vol. 22, no. 3, pp. 156-163, 2016.
4. H. El-Sayed and G. Thandavarayan, "Congestion detection and propagation in urban areas using histogram models," IEEE Internet of Things Journal, vol. 5, no. 5, pp. 3672-3682, 2018.
5. C. A. Tokognon, B. Gao, G. Y. Tian, and Y. Yan, "Structural health monitoring framework based on internet of things: A survey," IEEE Internet of Things Journal, vol. 4, no. 3, pp. 619-635, 2017.
6. K. M. Alam, M. Saini, and A. El Saddik, "Toward social internet of vehicles: Concept, architecture, and applications," IEEE access, vol. 3, pp. 343-357, 2015.
7 S. Tan, D. De, W.-Z. Song, J. Yang, and S. K. Das, "Survey of security advances in smart grid: A data driven approach," IEEE Communications Surveys & Tutorials, vol. 19, no. 1, pp. 397-422.
8. P. Maneenual and S. Vasupongayya, "Logging mechanism for internet of things: A case study of patient monitoring system," in 15th International Joint Conference on Computer Science and Software Engineering (JCSSE), 2018.
9. J. B. Welsh, "Role of continuous glucose monitoring in insulin-requiring patients with diabetes," Diabetes technology and therapeutics, vol. 20, no. S2, pp. S2-42, 2018.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An oral therapy tool, comprising:
   a mouthpiece including a first side and a second side, the mouthpiece defining a plurality of hollow chambers in an interior of the mouthpiece;
   a pressure sensor operatively connected to the mouthpiece; and
   a microcontroller in communication with the pressure sensor, the microcontroller configured to collect data relating to jaw strength, tongue position, and tongue movement based on user engagement with the mouthpiece while the oral therapy tool is in use and to communicate the data to a central computer server;
   wherein each of the hollow chambers is operably connected to the pressure sensor via a pressure-transmitting tubing.

2. The oral therapy tool of claim 1, wherein the pressure sensor comprises a plurality of pressure sensors, and wherein each of the plurality of hollow chambers is connected to a respective one of the plurality of pressure sensors.

3. A system for monitoring oral therapy, comprising:
an oral therapy tool, including
- a mouthpiece including a first side and a second side, the mouthpiece defining a plurality of hollow chambers in an interior of the mouthpiece;
- a pressure sensor operatively connected to the mouthpiece; and
- a microcontroller in communication with the pressure sensor, the microcontroller configured to collect data relating to jaw strength, tongue position, and tongue movement based on user engagement with the mouthpiece while the oral therapy tool is in use and to communicate the data to a central computer server,
- wherein each of the hollow chambers is operably connected to the pressure sensor via a pressure-transmitting tubing;

a central computer server in communication with the oral therapy tool; and
a database in communication with the central computer server, the database for storing data relating to a usage of the tool,
wherein a query of the data related to the usage of the tool can be initiated from a remote device and communicated to the remote device from the central computer server via a software application running on the remote device to thereby provide information relating to the usage of the tool to the remote device.

4. The system of claim 3, wherein the remote device is a mobile device.

5. The system of claim 3, wherein the remote device is a smart phone.

6. The system of claim 3, wherein the data relating to the usage of the device comprises session and/or minute-by-minute averages of an amount of pressure applied to the tool and/or a frequency of pressure applied to the tool.

7. A method for monitoring oral therapy, comprising:
collecting, via a central computer server, data from multiple oral therapy devices relating to a usage of the multiple oral therapy devices, each oral therapy device of the multiple oral therapy devices including
- a mouthpiece including a first side and a second side, the mouthpiece defining a plurality of hollow chambers in an interior of the mouthpiece;
- a pressure sensor operatively connected to the mouthpiece; and
- a microcontroller in communication with the pressure sensor, the microcontroller configured to collect data relating to jaw strength, tongue position, and tongue movement based on user engagement with the mouthpiece while the oral therapy tool is in use and to communicate the data to a central computer server;
- wherein each of the hollow chambers is operably connected to the pressure sensor via a pressure-transmitting tubing;

storing the data from the multiple oral therapy devices in a database;
analyzing, via the central computer server, the data stored in the database received from the multiple oral therapy devices to provide a recommended oral therapy regimen to a user based, at least in part, on the data from the multiple oral therapy devices;
wherein the data collected by the central computer server from each oral therapy device of the multiple oral therapy devices includes data relating to at least one of jaw strength, tongue position, and tongue movement based on user engagement with the mouthpiece of the oral therapy device.

8. The method of claim 7, and further comprising:
analyzing, via the central computer server, data related to the usage of one of the multiple oral therapy devices to determine an effectiveness of the one of the multiple oral therapy devices and associated oral therapy for the user; and
transmitting to a remote device the analysis of the data related to the usage of the one of the multiple oral therapy devices via a software application running on the remote device;
wherein the data related to the usage of the one of the multiple oral therapy devices includes data from the oral therapy device collected at a first time point and a second time point.

9. The method of claim 8, wherein analyzing the data related to the usage of the one of the multiple oral therapy devices comprises comparing the data at the first time point to the data at the second time point.

10. The method of claim 8, wherein the data relating to the usage of the one of the multiple oral therapy devices comprises session and/or minute-by-minute averages of an amount of pressure applied to the tool and/or a frequency of pressure applied to the tool.

11. The method of claim 8, wherein the remote device is a smart phone.

* * * * *